(12) United States Patent
Leong

(10) Patent No.: US 7,587,283 B2
(45) Date of Patent: Sep. 8, 2009

(54) GROWTH AND BASELINE IDENTIFICATION DETERMINATION FOR AMPLIFICATION DATA

(75) Inventor: Harrison M. F. Leong, San Francisco, CA (US)

(73) Assignee: Celera Corporation, Alameda, CA (US)

( * ) Notice: Subject to any disclaimer, the term of this patent is extended or adjusted under 35 U.S.C. 154(b) by 269 days.

(21) Appl. No.: 11/428,384

(22) Filed: Jul. 1, 2006

(65) Prior Publication Data

US 2008/0154511 A1    Jun. 26, 2008

(51) Int. Cl.
*G01N 33/48* (2006.01)
(52) U.S. Cl. ........................................ 702/19
(58) Field of Classification Search .............. 702/19
See application file for complete search history.

(56) References Cited

U.S. PATENT DOCUMENTS

2004/0096819 A1* 5/2004 McMillan et al. .............. 435/4
2005/0118620 A1* 6/2005 Vess ................................ 435/6
2006/0271308 A1* 11/2006 Lerner ......................... 702/19

* cited by examiner

*Primary Examiner*—Bryan Bui
*Assistant Examiner*—Jonathan Teixeira Moffat
(74) *Attorney, Agent, or Firm*—MH2 Technology Law Group LLP

(57) ABSTRACT

Aspects of the present invention describe a method and apparatus for automating analysis of genetic samples. The initial operation receives amplification data associated with at least one spectral species and a genetic sample in each well of a plate. A putative growth signal is identified for the genetic sample from the amplification data forming a baseline region having a start point and an end point along with a growth region. Depending one on one or more characteristics detected in the amplification data forming the baseline region and growth region, aspects of the present invention modifies the baseline region to further identify the putative growth signal.

6 Claims, 10 Drawing Sheets

GROWTH AND BASELINE IDENTIFICATION DETERMINATION FOR AMPLIFICATION DATA

CROSS-REFERENCE TO RELATED APPLICATIONS

This application is related to and has an effective filing date of Provisional Application No. 60/695,983, filed Jun. 30, 2005 assigned to the assignee of the present invention entitled, "Automated Ct Extraction from Amplification Data" by Harrison Leong which is incorporated herein by reference.

INTRODUCTION

Quantitative nucleic acid analysis is extensively used in biological research and clinical analysis. Some of the applications which make use of this technology include: measurement of gene expression, monitoring of biological responses to stimuli, genomic-level gene quantitation, and pathogen detection. Typically, these methodologies utilize Polymerase Chain Reaction (PCR) as a means for selectively amplifying nucleic acid sequences in a manner that allows for their detection.

While it is generally desirable to automate the quantitation process, conventional methodologies often require a degree of user input in the form of subjective interpretation and/or approximation. As a result these techniques may suffer from reduced accuracy and significant user-induced variability. Furthermore, in high-throughput applications where many samples are to be processed simultaneously, it is desirable to provide increased automation capabilities to improve the speed with which the analysis may be conducted. The aforementioned limitations of conventional techniques illustrate the need for an improved method for analyzing data generated by PCR-based quantitation techniques that may increase the potential for automation while improving the quantitative accuracy and reproducibility of the analysis.

BRIEF DESCRIPTION OF THE DRAWINGS

The skilled artisan will understand that the drawings, described below, are for illustration purposes only. The drawings are not intended to limit the scope of the present teachings in any way.

SUMMARY

Figure 1:
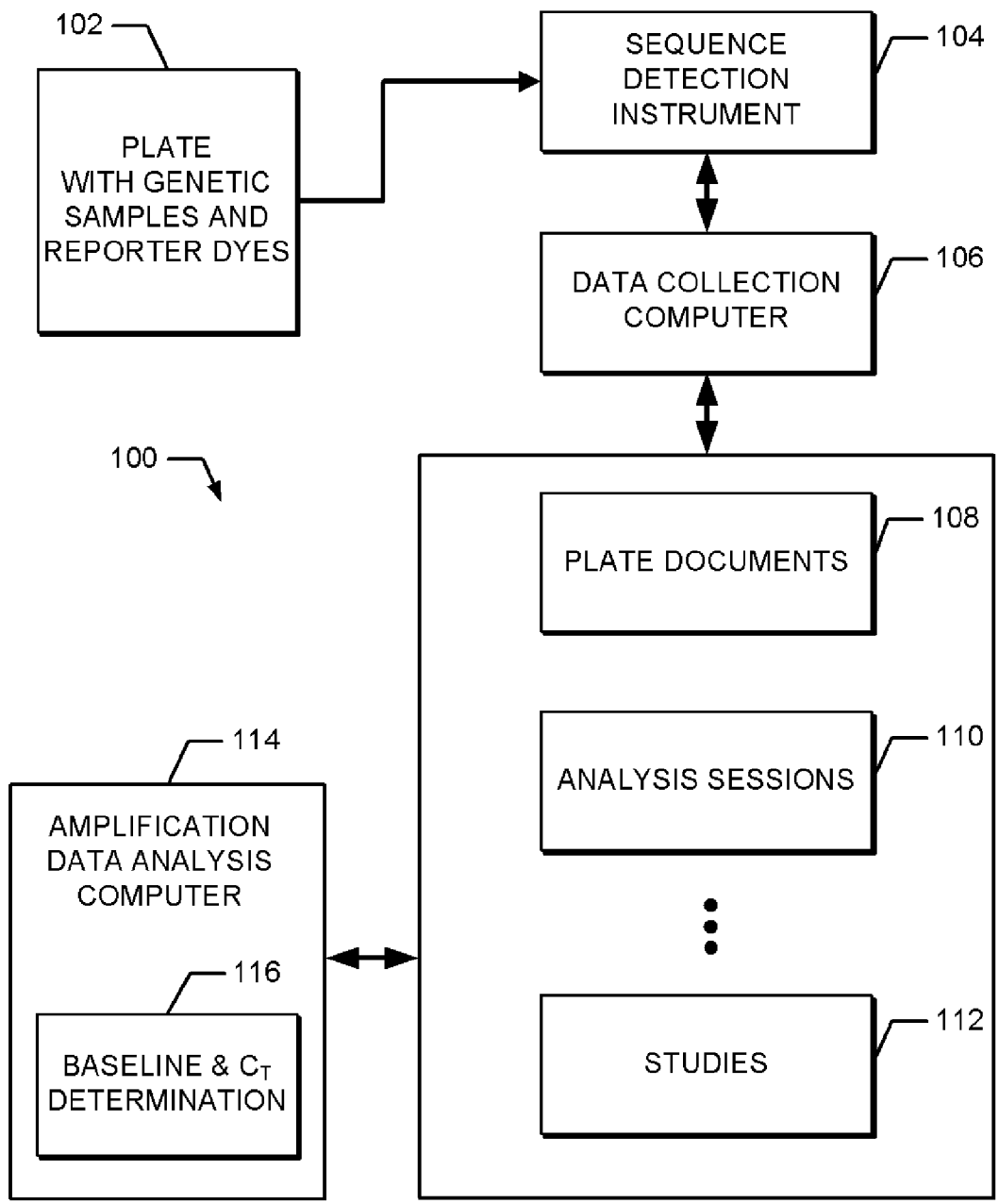
FIG. 1. is a schematic illustrating a system for spectral detection and analysis in accordance with some implementations of the present invention.

Aspects of the present invention describe a method and apparatus for automating analysis of genetic samples. The initial operation receives amplification data associated with at least one spectral species and a genetic sample in each well of a plate. A putative growth signal is identified for the genetic sample from the amplification data forming a baseline region having a start point and an end point along with a growth region. Depending one on one or more characteristics detected in the amplification data forming the baseline region and growth region, aspects of the present invention modifies the baseline region to further identify the putative growth signal.

These and other features of the present teachings are set forth herein.

DESCRIPTION

Reference will now be made to the drawings wherein like numerals refer to like elements throughout. As used herein, "target", "target polynucleotide", and "target sequence" and the like refer to a specific polynucleotide sequence that is the subject of hybridization with a complementary polynucleotide, e.g., a blocking oligomer, or a cDNA first strand synthesis primer. The target sequence can be composed of DNA, RNA, analogs thereof, or combinations thereof. The target can be single-stranded or double-stranded. In primer extension processes, the target polynucleotide which forms a hybridization duplex with the primer may also be referred to as a "template." A template serves as a pattern for the synthesis of a complementary polynucleotide (Concise Dictionary of Biomedicine and Molecular Biology, (1996) CPL Scientific Publishing Services, CRC Press, Newbury, UK). A target sequence for use with the present invention may be derived from any living or once living organism, including but not limited to prokaryote, eukaryote, plant, animal, and virus, as well as synthetic and/or recombinant target sequences.

Furthermore, in describing the invention, as used herein the polynucleotide sequence may refer to a polynucleotide chain of variable length and may comprise RNA, DNA, cRNA, cDNA, or other polynucleotide species including but not limited to analogs having other than a phosphodiester backbone. Furthermore, as used herein, "reaction interval" refers to a designated portion of a target amplification reaction and may be evaluated as a function of cycle number or reaction time. Additionally, as used herein, "intensity data" refers to a measured or observed signal generated during the amplification reaction which may be related to the amount of target in the reaction and may comprise fluorescent measurements, radiolabel measurements, electrical measurements, light emission measurements, and other types of signals and measurements generated and acquired during the amplification reaction.

In general, amplification of a target DNA strand by polymerase chain reaction (PCR) proceeds through a series of temperature regulated cycles using the activity of a thermostable enzyme and a sequence specific primer set. At an appropriate temperature, primers hybridize to portions of the DNA strand and the enzyme successively adds a plurality of nucleotide bases to elongate the primer resulting in the production of progeny (daughter) strands. Each progeny strand possesses a complimentary composition relative to the target strand from which it was derived and can serve as a target in subsequent reaction cycles.

When applying quantitative methods to PCR-based technologies, a fluorescent probe or other detectable reporter construct may be incorporated into the reaction to provide a means for determining the progress of the target amplification. In the case of a fluorescent probe, the reaction can be made to fluoresce in relative proportion to the quantity of nucleic acid product produced. The TaqMan® procedure (Applied Biosystems, Calif.) describes one such fluorescent methodology for performing quantitative PCR.

Briefly described, the TaqMan® system integrates the use of a detectable reporter construct which comprises both a fluorescent label molecule and a quencher molecule. As long as the reporter construct remains intact, fluorescent label molecule emissions are absorbed by the quencher molecule. During the amplification process, however, the reporter construct is cleaved and the quencher molecule is released allowing the fluorescent label molecule emissions to be detected. The quantity or intensity of observed fluorescence may then be correlated with the amount of product formed throughout the reaction. Using this information, the initial quantity of target present in the reaction may be determined. Additional information describing the principles and applications of quantitative PCR can be found in: Real Time Quantitative PCR, Genome Research, Cold Spring Harbor Laboratory Press, 1996 and PCR Technology: Principles and Applications for DNA Amplification. Karl Drlica, John Wiley and Sons, 1997.

One characteristic feature of quantitative PCR-based amplification is that, the reaction kinetics typically change over the course of the reaction with the amount of product formed not necessarily increasing in a constant manner. For example, during the earlier cycles of a PCR reaction there may be an approximate doubling of the nucleotide strands with each cycle (exponential amplification). In the later cycles of the reaction, however, the efficiency of the amplification process may be diminished resulting in non-exponential amplification. Some of the factors that may affect the amplification efficiency include limiting quantities or depletion of reagents and competition for reaction products. The aforementioned changes in reaction kinetics may result in difficulties in determining the initial target concentration without performing detailed analysis of the reaction profile. In one aspect it is desirable to monitor the reaction at various time or cycle intervals and acquire data which quantifies the emitted fluorescence of the reaction at these intervals. Using this information, data analysis methods may be used to assess the acquired fluorescence measurements and determine the initial concentration of target present in the reaction.

In quantitation methodologies, including real-time PCR, the fluorescence intensity for each amplification reaction may be determined using a charge-coupled device (i.e. CCD camera or detector) or other suitable instrument capable of detecting the emission spectra for the label molecules used in the reporter construct. Fluorescence samplings are performed over the course of the reaction and may be made at selected time intervals (for example: 25 millisecond samplings performed at 8.5-second intervals). In one aspect, emission spectra are measured for both the label molecule and the quencher molecule with the emission intensity resultant from the quencher molecule changing only slightly compared to that of the label molecule. The emission intensity of the quencher molecule may further be used as an internal standard to normalize emissions generated by the label molecule.

For each amplification reaction, the measured emission spectra obtained from the fluorescence samplings form an amplification data set that may be processed to determine the initial target concentration. In one aspect, the amplification data set comprises fluorescence intensity information obtained from a plurality of independent or coupled reactions. These reactions may be performed simultaneously or at different times wherein the data is accumulated and collectively analyzed. Furthermore, the amplification data set may further comprise fluorescence intensity data obtained from one or more standards whose initial target concentration is known.

In practice, the fluorescence signal generated during an amplification reaction may take on various characteristics associated with the chemical reactions involved and/or the instrumentation used to conduct/monitor the reaction. For example, it may be observed that gradual increases or decreases in signal level arise with increasing cycles. These signal level changes, however, may not necessarily be directly associated with the amplification of the target genetic material.

Additionally, the amplification profile for a selected reaction may reflect a sigmoid shape. In such instances, the increase in abundance of the target genetic material may slow and ultimately stop at some point due to chemical limitations. Furthermore, noise may be observed in the form of spikes or humps in the signal data. Such noise may be observed in earlier cycles, originating as high values followed by a decay to baseline. Noise may also take the form of steps in the approximate middle of the signal, up and down excursions, weak growth-like signals, and other forms. In such instances, the observed noise may have nothing to do with the growth of the target genetic material. In certain instances, the growth/amplification rate may be significantly slower than theoretical doubling or observed amplification may be represented by very early growth, within four or five cycles.

As will be described in greater detail hereinbelow, aspects of the present teachings describe a novel approach for automatically establishing the amplification profile for a reaction in view of chemical and other limitations. Improving the interpretation of the amplification data also can enhance estimations of Ct values from real-time PCR data and their use in genetic analysis.

Overall, this approach may be helpful in addressing the aforementioned characteristics of the amplification data as well as increase the sensitivity and specificity of instrumentation such as the ABI PRISM 7000 (Applied Biosystems, Foster City Calif.) used in quantification assays. An exemplary software package used in connection with this instrument that may be configured to implement the disclosed analytical approaches is the "Sequence Quantification Software Package" (Applied Biosystems, Foster City Calif.). Additional details describing this package may be found in the User's Guide: Sequence Quantification Software v3.0 PN: 5001194 which is incorporated by reference.

The methods described herein represent a potential advance over existing approaches improving performance with regards to avoiding false positives and false negatives. Moreover, this facilitates a more reliable positive identification of bona fide growth and producing an estimated Ct value with low variability. In one aspect, false positives and false negatives may arise from inaccurate baseline determination. False positives may also arise from dye bleedover and/or crosstalk. In such circumstances, thresholds for determining Ct values may be set too high to capture signals of low-concentration samples. An advance over conventional approaches provided by the present teachings improves performance by accurately assessing the portion of the amplification signal that should be taken to be the baseline. Additionally, the present teachings may be used to distinguish crosstalk and/or bleedover from a bona fide amplification signal. The methods described also provide the ability to accommodate a wider range of amplification signals.

FIG. 1 is a schematic illustrating a system for spectral detection and analysis in accordance with some implementations of the present invention. System 100 includes a plate 102 with genetic samples, a sequence detection instrument 104, a data collection computer 106, plate documents 108, analysis session 110, studies 112 containing analytical results from many plates and a amplification data analysis computer 114. To improve the quality of information being processed, sequence data analysis computer 114 further utilizes one or more baseline and Ct determination approaches 116 to automate the analysis of the data using information from the plate documents 108, analytical sessions 110, and the studies 112 that were obtained from the genetic samples in plate 102.

Sequence detection instrument 104 includes a spectral detector capable of distinguishing certain spectral species emitted from the fluorescence of reporter dyes interacting with the genetic material in wells on plate 102. The spectra is typically monitored in real-time as a thermal cycler in the sequence detection instrument 104 performs PCR on the genetic material. For example, PCR operations may cause the sample or target genetic material to replicate and hybridize with increasing amounts of a SYBR green dye detectable in the wells of plate 102. After several thermal cycles, the concentration of the target increases along with a detectable rapid increase of fluorescence from the SYBR green dye or other reaction substrate. A cycle threshold or Ct measurement is then identified when the measure of fluorescent intensity increases linearly on a logarithmic scale compared with the increasing cycle number. Subsequent analysis of Ct values among various reactions may be used to identify a concentration of the target genetic material.

Data collection computer 106 gathers raw data provided by sequence detection instrument 104 and stores in plate documents 108 as required by a particular study or experiment being performed. The raw data is labeled, organized and stored by data collection computer 106 in one of several different storage areas or files for subsequent processing. For example, the example in FIG. 1 depicts data collection computer 106 as capable of storing the raw data in as plate documents 108 or studies 112. In some cases, data collection computer 106 may also perform certain calibration operations or other types of basic data analysis with the results to be stored in analysis sessions 110.

Resulting data stored in plate documents 108, studies 112 and analysis sessions 110 are then made available to sequence data analysis computer 114. Operations in amplification data analysis computer 114 not only may perform baseline and Ct determination but improves computational analysis associated with genetic analysis. In particular, aspects of the present invention provide automated baseline and Ct determination operations 116 for increasing throughput of analysis while improving accuracy.

Figure 2:
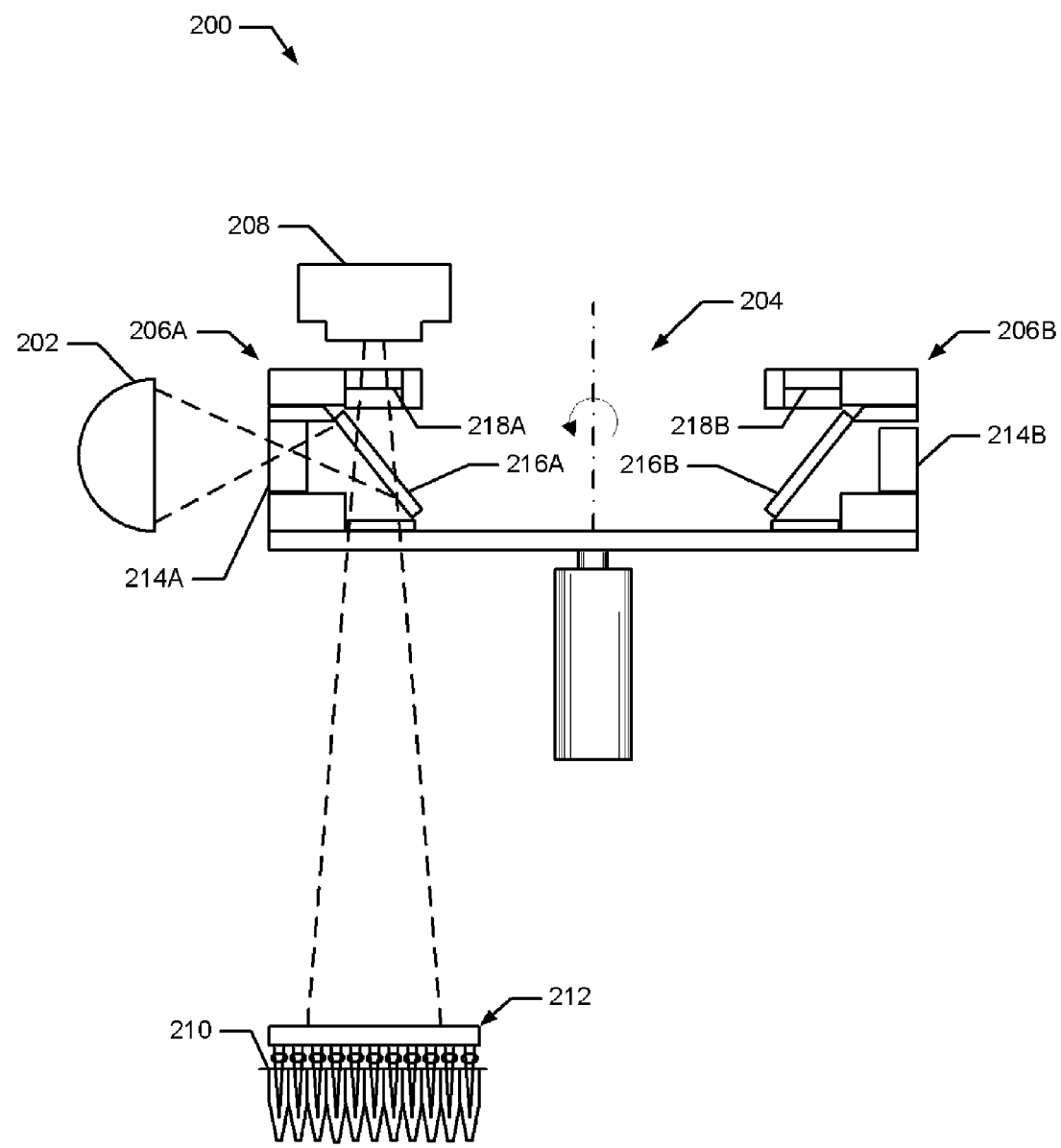
FIG. 2 is a schematic illustration of a system used for fluorescent signal detection in accordance with implementations of the present invention.

FIG. 2 is a schematic illustration of a system 200 used for fluorescent signal detection in accordance with implementations of the present invention. This illustration depicts certain features typically associated with the Applied Biosystems 7500 Real-Time PCR System. However, aspects of the present invention should not be limited by any one or several features associated with this equipment. Consequently, various aspects of the invention can be used in conjunction with the Applied Biosystems 7900HT Fast Real-Time PCR System model as well as almost any other device involved with gathering and/or analyzing spectra from a genetic sample.

Accordingly, detection system 200 illustrates some of the components making up spectral detector and optics in sequence detection instrument 104 previously described in FIG. 1. Detection system 200 can be used with real-time PCR (RT-PCR) processing in conjunction with aspects of the present invention. As illustrated, detection system 200 includes a light source 202, a filter turret 204 with multiple filter cubes 206, a detector 208, a microwell tray 210 and well optics 212. A first filter cube 206A can include an excitation filter 214A, a beam splitter 216A and an emission filter 218A corresponding to one spectral species selected from a set of spectrally distinguishable species to be detected. A second filter cube 206B can include an excitation filter 214B, a beam splitter 216B and an emission filter 218B corresponding to another spectral species selected from the set of spectrally distinguishable species to be detected.

Light source 202 can be a laser device, Halogen Lamp, arc lamp, Organic LED, an LED lamp or other type of excitation source capable of emitting a spectra that interacts with spectral species to be detected by system 200. In this illustrated example, light source 202 emits a broad spectrum of light filtered by either excitation filter 214A or excitation filter 214B that passes through beam splitter 216A or beam splitter 216B and onto microwell tray 210 containing one or more spectral species. Further information on light sources and overall optical systems can found in U.S. Patent Application 20020192808 entitled "Instrument for Monitoring Polymerase Chain Reaction of DNA", by Gambini et al. and 200438390 entitled "Optical Instrument Including Excitation Source" by Boege et al. and assigned to the assignee of the present case.

Light emitted from light source 202 can be filtered through excitation filter 214A, excitation filter 214B or other filters that correspond closely to the one or more spectral species. These spectrally distinguishable species may include one or more of FAM, SYBR Green, VIC, JOE, TAMRA, NED, CY-3, Texas Red, CY-5, Hex, ROX (passive reference) or any other fluorochromes that respond by emitting a detectable signal. In response to light source 202, the target spectral species and selected excitation filter, beamsplitter and emission filter combination provide the largest signal response while other spectral species with less signal in the bandpass region of the filters contribute less signal response. Multicomponent analysis is typically used to determine the concentration of the individual species according to their respective contribution to the emitted spectra.

Referring to FIG. 2, microwell tray 210 generally contains the genetic target sample with one or more reporter dyes corresponding to the assay used in conjunction with an experiment. Microwell tray 210 can include a single well or any number of wells however typical sets include 96-wells, 384-wells and other well configurations. Of course, experiments may be designed to use many other plate configurations having different multiples of wells other than 96. The sample and particular combination of dyes used in the selected assay may be sealed in microwell tray 210 using heat and an adhesive film to ensure they do not evaporate or become contaminated.

Detector 208 receives the signal emitted from spectral species in microwell tray 210 in response to light passing through the aforementioned filters. Detector 208 can be any device capable of detecting fluorescent light emitted from multiple spectrally distinguishable species in the sample. For example, detector 208 can be selected from a set including a charge coupled device (CCD), a charge induction device (CID), a set of photomultiplier tubes (PMT), photodiodes and a CMOS device. Information gathered by detector 208 can be processed in real-time in accordance with implementations of the present invention and through subsequent post-processing operations.

Figure 3:
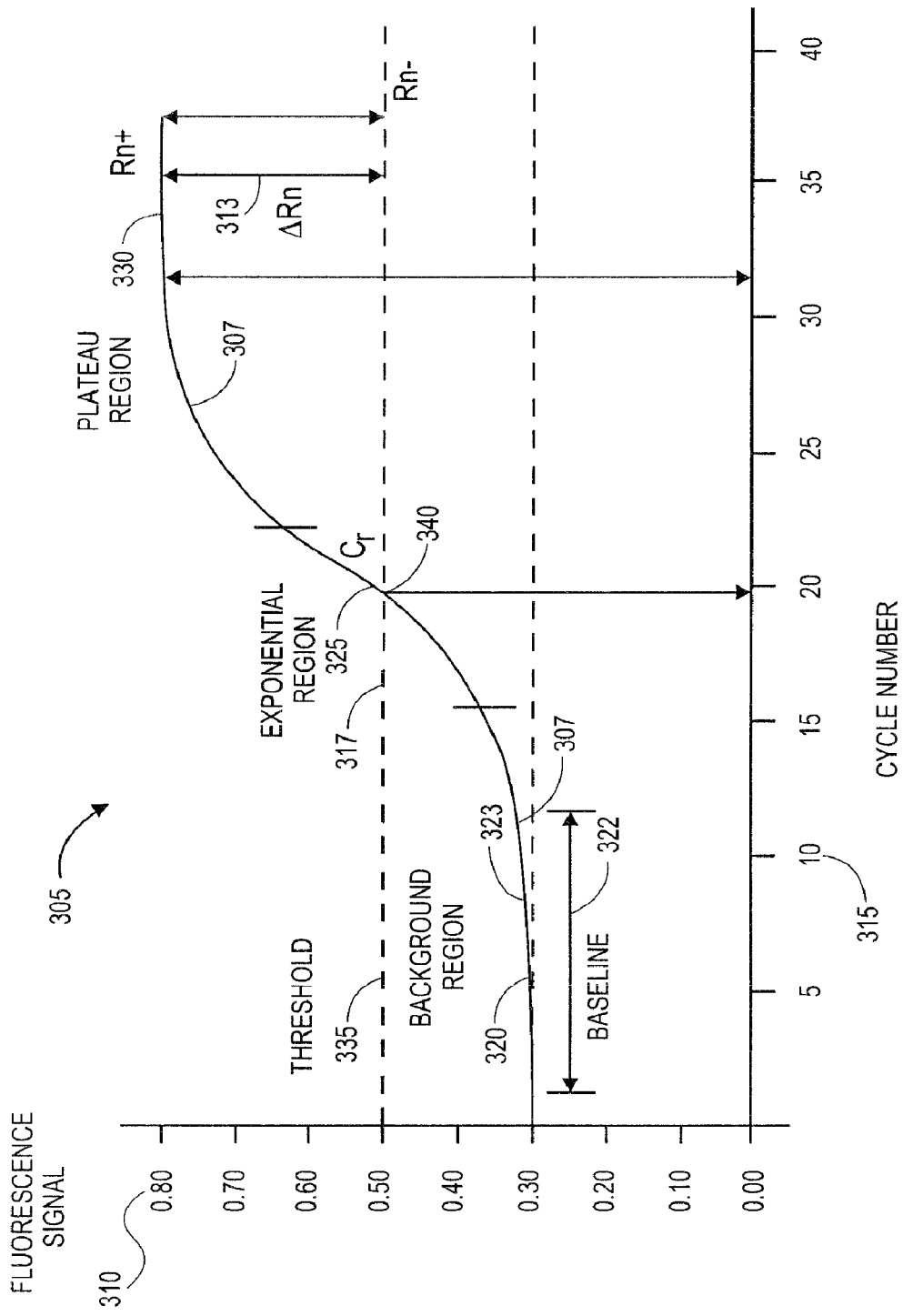
FIG. 3 illustrates an amplification plot depicting the reaction characteristics for an exemplary nucleic acid target and the various analytical components that may be used to quantify the target.

FIG. 3 illustrates an amplification plot 305 depicting the reaction characteristics for an exemplary nucleic acid target and the various analytical components that may be used to quantify the target. It will be appreciated that the amplification plot 305 is shown for the purposes of explanation and need not necessarily be constructed directly to apply the quantitative methods of the invention. However, the system can be configured to present a graphical representation of the amplification data set to aid a user in visualizing the results of the analysis.

The amplification plot 305 comprises a plurality of data points 307 forming an amplification profile 317 which is indicative of the measured intensity of signal generated by the label molecules within the amplification reaction. In the amplification plot 305, the y-axis values 310 correspond to observed signal intensities generated over the course of the amplification reaction. In one aspect, these signal intensities may correspond to fluorescent emissions obtained from instrumental sampling using a charge-coupled device or similar apparatus. Furthermore, the fluorescence detector may be configured to monitor wavelengths from approximately 500 to 650 nm. The x-axis values 315 correspond to the sample interval (shown as a function of cycle number) for the amplification reaction for which the signals are observed. Illustrated in this manner, the information represents the reaction progression as a function of the observed fluorescence intensities over the sampling interval and may be used to monitor the synthesis of progeny nucleic acid strands from an initial sample target.

When analyzing the amplification profile 317, various regions are identified and used in calculations for determining the initial concentration of target present in the reaction. Conventional genetic analysis methodologies generally require at least a degree of subjective interpretation. This subjective limitation often necessitates visually inspecting intensity data in order to identify these relevant regions of amplification profile 317. The effect of this subjective and somewhat manual approach to analysis may decrease the accuracy of quantitative analysis and their results, as well as, increase the analysis time.

In one aspect, the system and methods described herein overcome some of the limitations and drawbacks associated with conventional methodologies through the implementation of an analysis strategy that identifies significant regions of the amplification profile 317 in an objective and reproducible manner. As a result, aspects of the invention may improve the accuracy of quantification when determining the initial concentration of target present in an amplification reaction.

As shown by way of example in FIG. 3, the results from a typical quantitation reaction can be characterized by different regions 320, 325, 330 within, the amplification profile 317 corresponding to a background (noise) region 320, an exponential region 325, and a plateau region 330. During the earlier cycles of the reaction, the observed fluorescence produced by the label generally does not substantially exceed that produced by the quencher. Fluorescent emissions measured during these cycles are generally very low and may fall below the detection limits or sensitivity of the data acquisition instrumentation.

Furthermore, non-specific florescence arising from instrumental variations or noise within this background region 320 may significantly contribute to the observed signal. This may make it difficult to accurately determine the emission fluorescence arising from amplification in the early cycles of the reaction. Accordingly, implementations of the present invention more accurately identify reaction fluorescence data falling in background region 320 to improve overall quantitation. For example, it may be desirable to accurately identify the range and bounds of the background region 320 so that this portion of the amplification reaction may be distinguished from exponential region 325 or plateau region 330 from amplification profile 317. Aspects of the present invention contemplate that proper identification of background region 320 contributes to a more accurate measure of fluorescence in other regions and improved quantitation in other areas of the analytical process.

In one implementation, sub-region within the background region 320 may be identified as a baseline data set 322 and used in characterizing and analyzing background region 320. Baseline data set 322 serves as an indicator of the relative level of background fluorescence or noise from which exponential region 325 may be differentiated. As will be described in greater detail herein below, construction of the baseline 323 provides for the ability to quantify the relative noise present in the amplification reaction. Baseline 323 also can be used to normalize data points 307 of amplification profile 317 and partially compensate for the noise.

Exponential region 325 covers the region of amplification profile 317 that follows background region 320. It is within this portion of amplification profile 317 that the observed and measured intensity of fluorescence should increase exponentially (ie., doubling sample concentration at each cycle). Within the exponential region 325, the detected quantity of fluorescence is typically sufficient to overcome noise that may predominate in the background region 320. The characteristics of the amplification reaction during the cycles associated with the exponential region 325 further reflect desirable reaction kinetics that can be used to perform quantitative target calculations. Together, both exponential region 325 and even plateau region 330 are sometimes referred to as part of "a growth region" since corresponding data points 307 generally exhibit a trend of substantially increasing or progressive fluorescence.

It will be appreciated that the increase in target concentration within the exponential region 325 need not necessarily follow a substantially exponential rate. Instead, this region 325 of the amplification profile 317 may be substantially characterized by a sub-exponential, geometric, linear and/or progressive rate of increase in target concentration. More generally, the amplification region 325 may be characterized as the portion of the amplification profile 317 where an increased rate of target accumulation may be observed relative to earlier and later cycles of the reaction. It will be appreciated that the methods described herein are suitable for assessing amplification reactions having a wide variety of characteristic increases in target concentration. For example, an increased rate of accumulation for a target should not be limited exclusively to assessing regions of "pure" exponential increase.

Delineation of discrete regions within the amplification profile 317 is useful for distinguishing characteristic reaction kinetics and further identifying portions of the amplification profile amenable to quantitation calculations. It will be appreciated by one of skill in the art that specific designation of these regions is not required to perform the quantitative calculations described herein.

It will further be appreciated that the characteristics of these regions may vary from one reaction to the next and may deviate significantly from illustrated profile. For example, in some amplification reactions, the exponential region 325 may extend over a different range of cycles and possess different intensity characteristics. Likewise, the background region 320 and the plateau region 330 may possess unique characteristics for each reaction. Additionally, other regions within the amplification profile 317 may be identifiable, for example, a region of substantial linearity may follow the exponential region 325. As will be described in greater detail hereinbelow, the quantitation methods may be desirably "tuned" or customized to accommodate potentially diverse classes of amplification profile characteristics.

The analytical approach used to quantitate the initial target concentration is based, in part, upon the identification of a threshold 335. In one aspect, the threshold 335 desirably aids in identifying and delineating noise present in the background region 320 and furthermore intersects with the amplification profile 317 at some point. The point of intersection between the threshold 335 and the amplification profile 317 is identified by a threshold cycle 340 or CT 340. ($C_T$) $C_T$ represents the cycle number and fluorescence intensity when the amplitude profile 317 intersects with threshold 335. As will be appreciated by one skilled in the art, accurately determining $C_T$ 340 is important as it likely influences subsequent calculations to predict the initial quantity or concentration of target present in the reaction.

FIG. 4A through 4H depict one or more characteristics of an amplification profile that may be accommodated using implementations of the present invention. While many more amplification profiles were contemplated, this selection of amplification profiles 4A through 4H each highlight one or several different conditions or characteristics that may affect the amplification data and the corresponding plot of the data. In practice, it is contemplated that more than one of these conditions or other anomalies may also occur and influence the amplification profile.

Figure 4A:
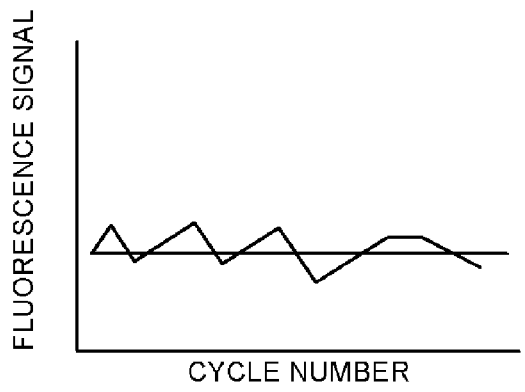
FIGS. 4A to 4H depict one or more characteristics of an amplification profile that may be accommodated using implementations of the present invention.

For example, FIG. 4A illustrates a zero crossing approach used to identify a putative a signal as actually being noise. The zero crossing approach measures a frequency that the amplification signal in FIG. 4A crosses above and below a zero point without showing growth. To refine and improve this method, additional measurements may include the height or depth of the crossings compared with other similarly generated signals. If there are sufficient crossings of a 'zero' boundary point then the zero crossing approach may lead to elimination or non-use of certain data considered to be noise rather than signal.

Figure 4E:
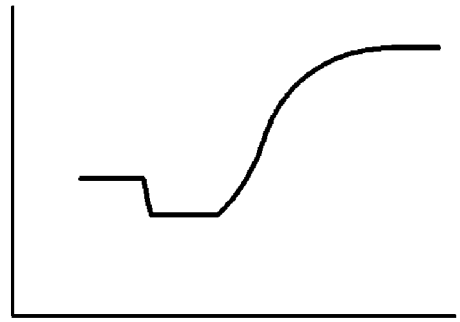
Figure 4B:
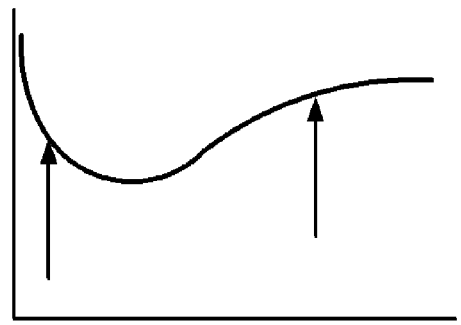

FIG. 4B illustrates an anomalously high amplitude during early cycles and a rapid drop to much lower baseline level. Detecting excursions in the amplification data may occur during earlier cycles of the amplification reaction and determined by observing deviations from a median across selected cycles. If such excursions are detected, then the baseline may be repositioned or started at a higher cycle.

Figure 4F:
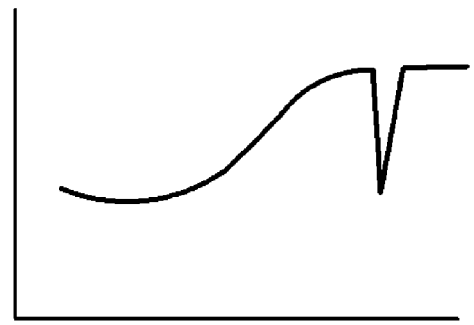
Figure 4C:
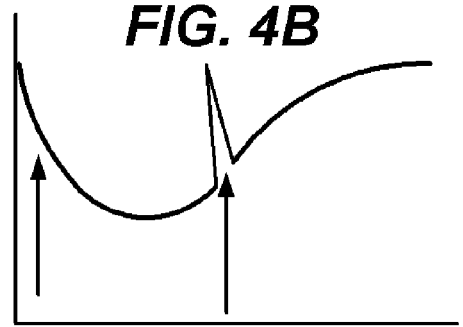

FIG. 4C illustrates a combination of an anomalously high amplitude during early cycles and a rapid spike in the amplification data during the growth phase of the genetic sample. In this case, aspects of the present invention would identify and avoid the rapid spike in intensity and continue processing. The anomalously high amplitude during early cycles may also be obviated again by repositioning the starting point of the base line to a higher cycle.

Figure 4G:
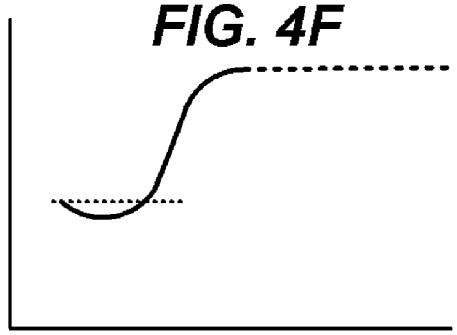
Figure 4D:
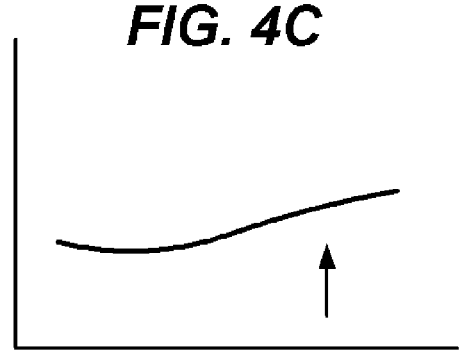

FIG. 4D illustrates a non-exponentional or low growth in the amplification or growth portion during later cycles. It is possible that the assay used did not function properly or the genetic sample is, for some reason, not experiencing proper growth during the growth phase. If it is possible, aspects of the present invention may move the end point of the baseline region to higher cycles or determine the data is noise and not signal as originally assumed.

FIG. 4E illustrates a step in the baseline region. Aspects of the present invention may move the start point of the baseline region to a higher cycle to ensure the baseline region has a substantially flat or zero slope.

FIG. 4F illustrates exponentional growth in the amplification or growth portion but an anomalous rapid drop off in later cycles. Detecting negative-going "spikes" in the growth phase of the amplification signal by identifying negative amplitude changes for a selected threshold. Further, baseline endpointing is performed in such a manner so as to avoid being located on such spikes. In one aspect, a baseline endpoint may be located on a spike and the endpoint may be relocated to a lower (or higher) cycle.

FIG. 4G illustrates an exponential growth in the amplification but a relatively short baseline region. Aspects of the present invention may move the end point of the baseline region to a lower cycle to ensure the baseline region has a substantially flat or zero slope.

Figure 4H:
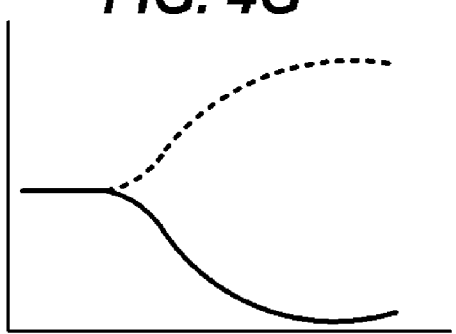

FIG. 4H illustrates an amplification curve growing in the negative amplitude direction. Aspects of the present invention can properly detect the appropriate baseline endpoint for growth signals in the negative amplitude direction. The analysis is agnostic to the orientation of the growth portion of the signal. For example, one implementation rotates the negative portion of the curve into a positive amplitude region. Keeping the growth region in the proper quadrant allows the information to be processed and analyzed.

Figure 5:
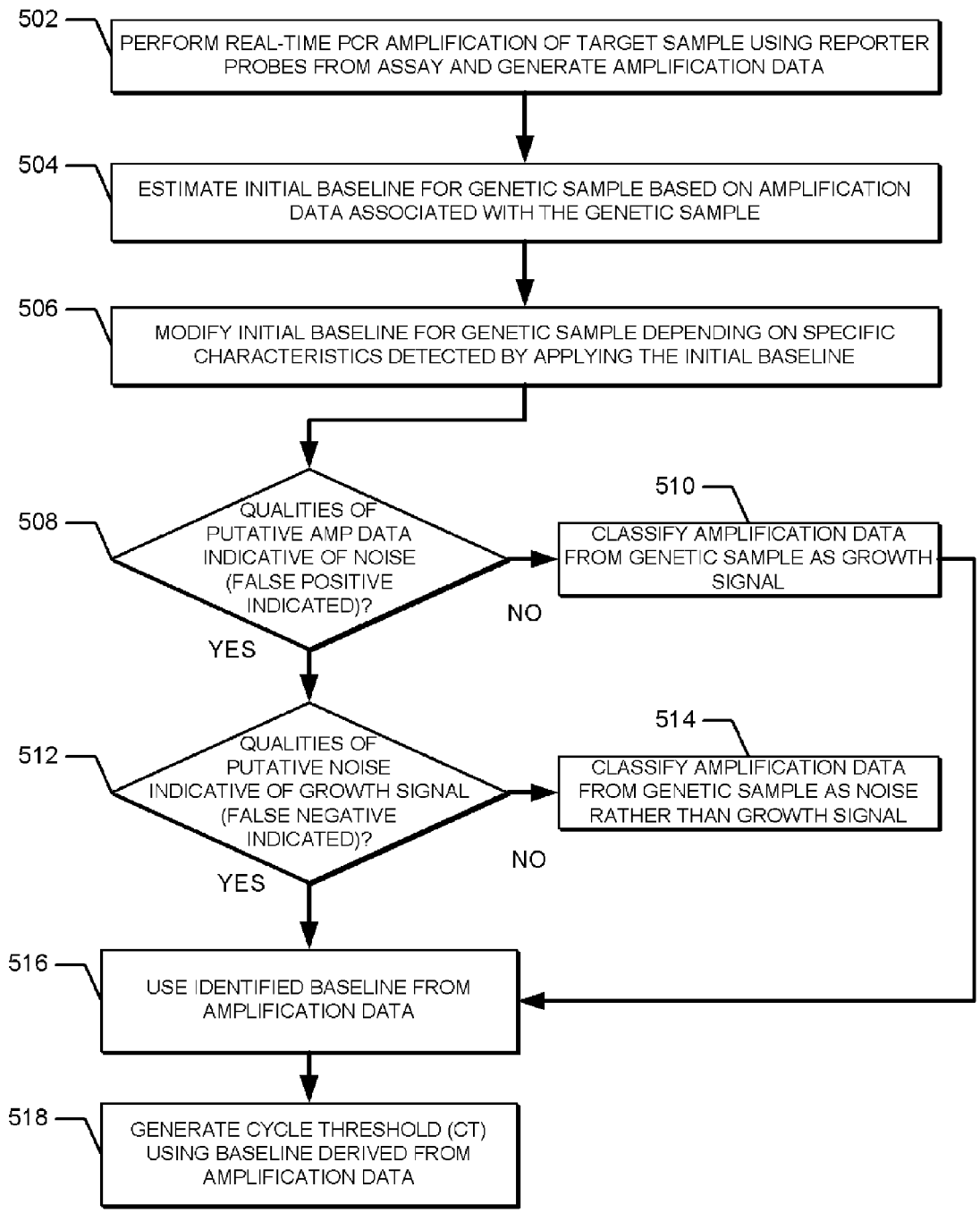
FIG. 5. depicts a flow chart diagram of the operations used to automatically verify amplification data for a genetic sample in accordance with aspects of the present invention.

FIG. 5 depicts a flow chart diagram of the operations used to automatically verify amplification data for a genetic sample in accordance with aspects of the present invention. Depending on the implementation, one or more of the operations in FIG. 5 may be used to automatically analyze and verify amplification data for improved accuracy and determination of a cycle threshold ($C_T$). It is contemplated that one implementation uses the operations outlined and ordered as depicted however alternate implementations may alter the order of operations as well as eliminate or insert operations as needed by the particular implementation. Each of the various operations presented and described herein may alone or in combination with other operations improve the determination of Ct and other critical values including a starting quantity of genetic material.

Initially, aspects of the present invention performs real-time PCR amplification of the target sample using reporter probes from an assay and generates amplification data (502). As previously described, each reporter probe has both a fluorescent label molecule and a quencher molecule. While the reporter construct remains intact fluorescent label molecule emissions are absorbed by the quencher molecule. During the amplification process, however, the reporter construct is cleaved and the quencher molecule is released allowing the fluorescent label molecule emissions to be detected and stored as amplification data.

Alternate implementations may also be applied to many other related technologies other than conventional report probes. For example, aspects of the present invention would also applies to molecular beacons, a technology where quencher and reporter dye are close together when unattached to the genetic sample of interest but become far apart when attached to genetic material being amplified. Generally, various aspects of the invention are contemplated to apply to any signal response having some linear baseline followed by exponential increase and a gradual plateau.

Next, aspects of the present invention identify an initial baseline and growth region for the genetic sample based on the amplification data collected (504). One implementation of present invention estimates the initial baseline by first identifying a maximum amplitude in the amplification data using the signal amplitude detected in the last cycle of the PCR process or the peak signal amplitude found in any cycle. In either case, a fraction of the maximum amplitude selected is used as a threshold level and the latest cycle for which the data intersects this threshold is the initial estimate of the baseline end point.

It is contemplated by various implementations that sensitivities to signal anomalies inherent in the process of amplifying genetic material and monitoring the amplification process using fluorescent dyes can diminish the accuracy of estimating the boundaries of the baseline region. Aspects of the present invention resolve this by successively refining estimates of baseline region boundaries for the genetic sample depending on various specific characteristics detected in the data (506). A few of these anomalies were illustrated and described in FIG. 4A through 4H yet there are many other conditions and characteristics accommodated by implementations of the present invention. In each case, the anomalies are obviated by repositioning the baseline start and end points. Further details on dealing with anomalies are provided later herein.

Even with baseline region properly determined, it is also sometimes difficult to distinguish growth signals from other signals generated by processes other than growth of the target genetic material. Accordingly, aspects of the present invention may apply a collection of operations to distinguish growth signals from noise.

In one implementation, these operations test various qualities of the putative amplification for indication of noise rather than growth signal (508). This may be referred to as identifying a false positive as the amplification data initially appears as growth signal but further analysis reveals the data may instead be noise. Implementations of the present invention attempt to classify the amplification data from the genetic samples as growth signal. (510). Details of identifying false positives in accordance with one implementation are described later herein in conjunction with FIG. 8.

Another set of operations are applied if the amplification data is potentially seen as noise as a result of these tests. In particular, aspects of the present invention determine if the qualities of putative noise are actually indicative of growth signals (512). These operations check for a false negative identification of noise when in fact the amplification data information corresponds to growth signal and not noise. If the presence of noise is verified, this amplification data from the genetic sample is classified as noise and generally excluded from further analysis and processing (514). To preserve the information, the noise may be marked as such in a database or a baseline end point can be set to the last cycle essentially providing no information concerning growth to subsequent analysis routines.

Once the putative amplification data is analyzed, the resulting identified baseline is used (516) in further genetic analysis. In accordance with one or more implementations of the present invention, the estimated baseline derived from the amplification data is used to compensate non-zero amplification data in the baseline region. This operation is the prerequisite to obtaining a $C_T$ value (518) and other important measurements useful in genetic analysis.

Figure 6:
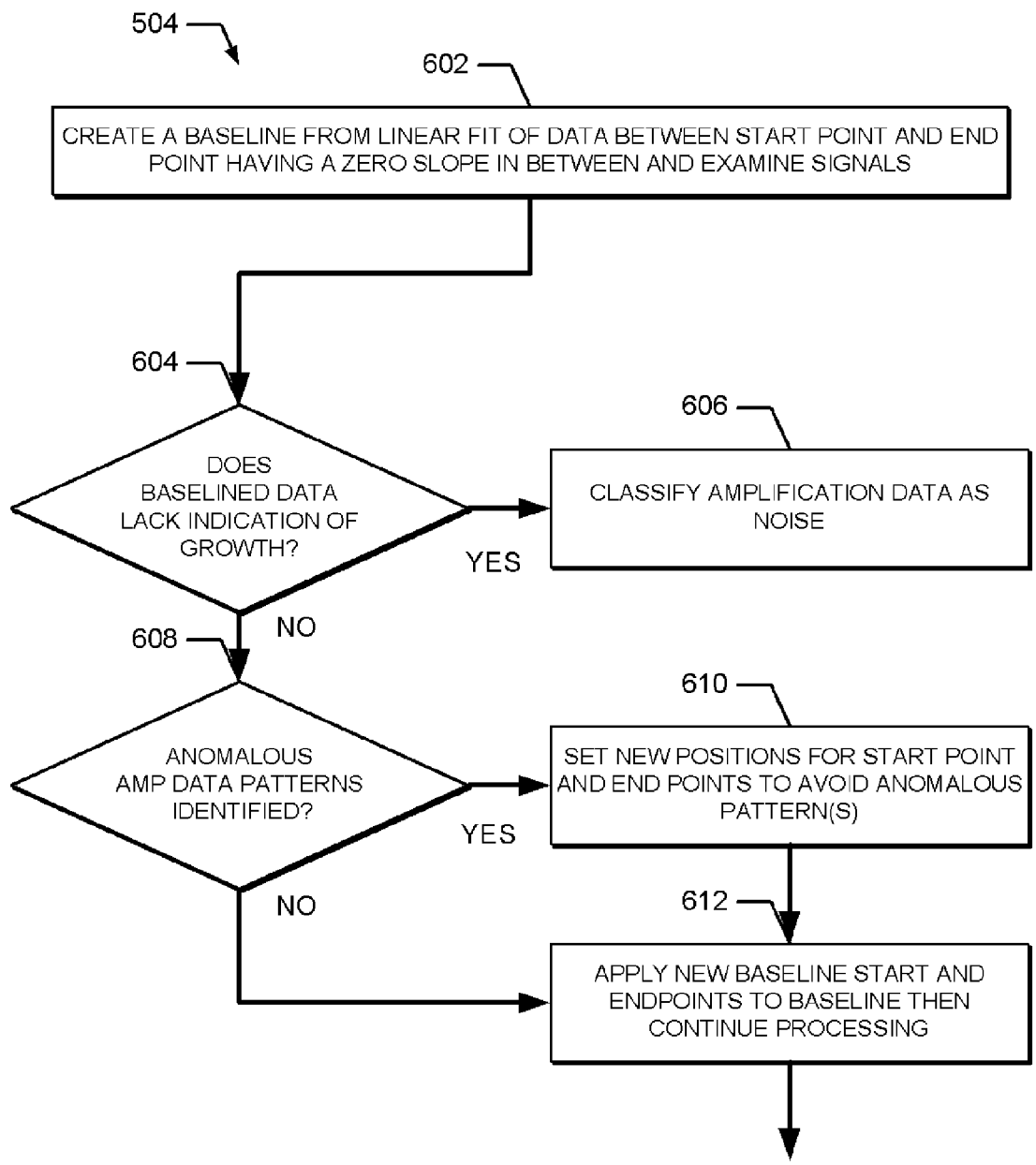
FIG. 6. is another flowchart diagram of operations to identify amplification likely considered noise as well as remove elements most likely considered anomalous data patterns in accordance with one implementation of the present invention.

FIG. 6 is another flowchart diagram of operations to identify amplification likely considered noise as well as remove elements most likely considered anomalous data patterns. These operations further detail operation 506 in FIG. 5. As previously described, one or more methods can be used to identify an initial baseline region from the amplification data. One implementation estimates the end of the baseline region by finding a data point at which signal amplitude is substantially lower than a peak amplitude of the amplification data. An implementation of the current invention creates a baseline by fitting a line to the data falling between the start and end points and delineates the baseline region. This line is then used to adjust the data so that, between the start and end points the data has a low slope or zero. (602)

The baselined data can be examined to determine whether that data lacks an indication of grown (604). If an indication of growth is lacking, the amplification can be classified as noise (606). In the event the amplification data appears to have growth signal, aspects of the present invention examines the data for anomalous data patterns (608). For example, anomalous data patterns may include a sudden spike up or a sudden spike down in either the baseline or growth regions. It is recognized that certain anomalous data pattern may be readily detected. In these cases, start points and end points of the baseline region are adjusted to avoid the anomalous data (610). Eventually, the new baseline start point and end point are applied and processing continues (612).

Figure 7:
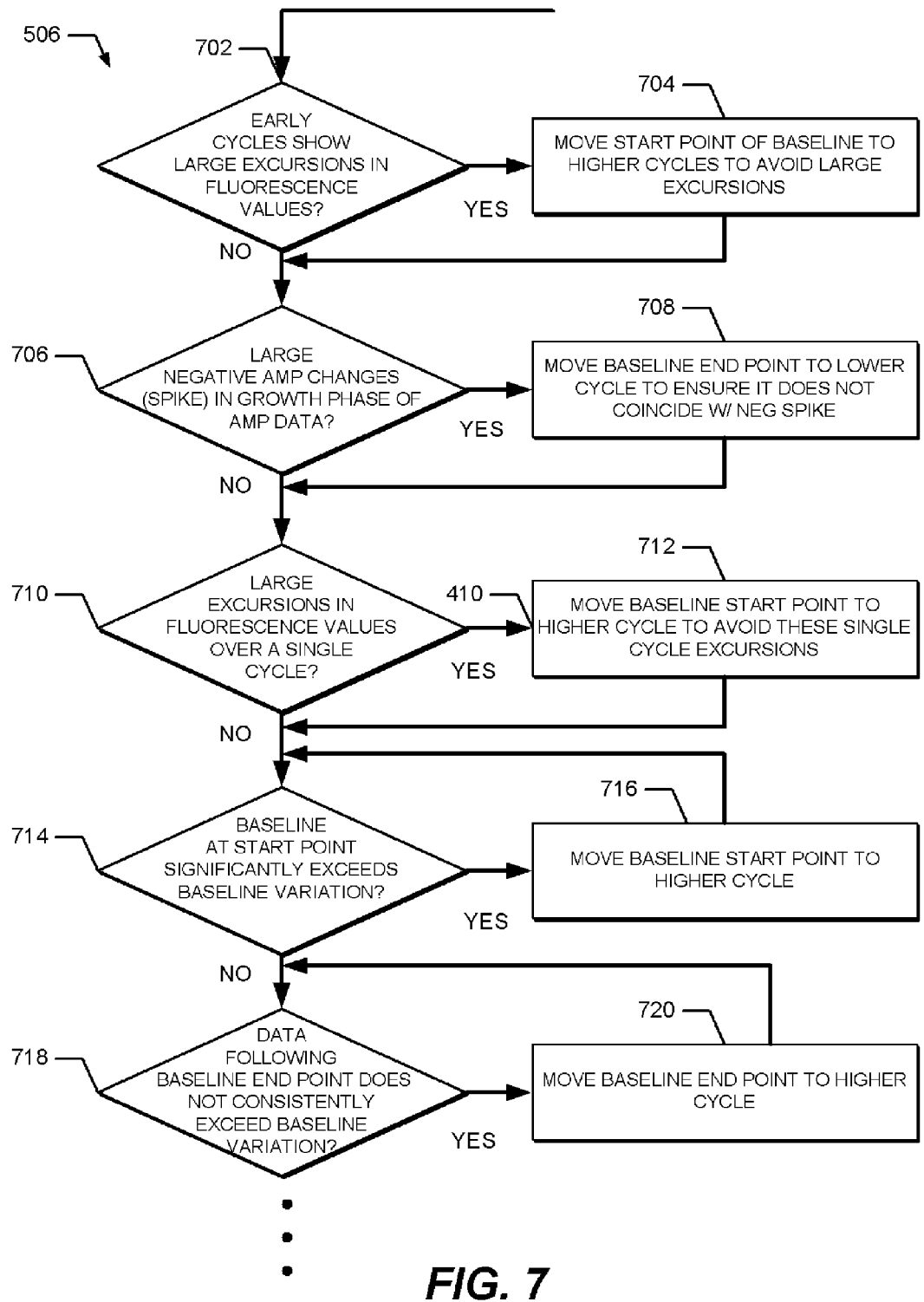
FIG. 7 is another flowchart diagram of operations to refine the boundaries of the baseline region in accordance with aspects of the present invention.

FIG. 7 is another flowchart diagram of operations to refine the boundaries of the baseline region in accordance with aspects of the present invention. One implementation makes these modifications of the baseline region in view of characteristics found in the amplification data and the initial estimate of the baseline region. One or more of the operations in FIG. 7 may be used to automatically analyze and verify amplification data for improved accuracy and determination of a cycle threshold ($C_T$). It is contemplated that one implementation uses the operations outlined and ordered as depicted however alternate implementations may alter the order of operations as well as eliminate or insert operations as needed by the particular implementation. Each of the various operations presented and described herein may alone or in combination with other operations improve the determination of Ct and other critical values including positioning of a baseline and starting quantity of genetic material.

In this example, implementations of the present invention checks if early cycles exhibit large excursions in fluorescence values (702). High fluorescence values at early cycles are not associated with amplification of the genetic material. One implementation moves the start point of baseline region to higher cycles thus avoiding these large excursions in the early cycles (704).

Next, aspects of the present invention checks for large negative amplitude changes (i.e., negative spikes) in the growth phase of the amplification data (706). Taken alone, this type of data also typically represents anomalous data that should be avoided or ignored and is depicted in FIG. 4E for reference. Aspects of the present invention accommodates the situation by shifting the baseline end point to a lower cycle and ensures it does not coincide with the negative spike (708).

Similarly, aspects of the present invention also check for large excursions in fluorescence values over a single cycle (710). At any given cycle, the amplitude variation should at most double and remain on a relative continuous trajectory. Sudden changes in amplitude and discontinuities indicate anomalous data and the need to refine the baseline region. For example, aspects of the present invention may move the baseline starting point to higher cycles to avoid these single cycle excursions (712).

Another measurement checks if the fluorescence value at the start point of the baseline region significantly exceeds the variation of fluorescence in the baseline (714). An example of this anomaly is illustrated and described in conjunction with FIGS. 4B and 4C. By moving the baseline start point to a higher Cycle (716), this early anomaly is obviated and lends to greater accuracy in determining the bounds of the baseline region and, hence, the accuracy of C.sub.T determination.

To find the cycle at which the baseline ends, the present invention implements an iterative algorithm that moves the baseline end point to a higher cycle (718) until the fluorescence values following the endpoint consistently exceed the variation of fluorescence in the baseline (720). Of course, the aforementioned operation is merely illustrative and it is contemplated that many other tests may be included that consider the characteristics of an initial baseline and the data that follows it as feedback for repositioning the baseline start and end.

Figure 8:
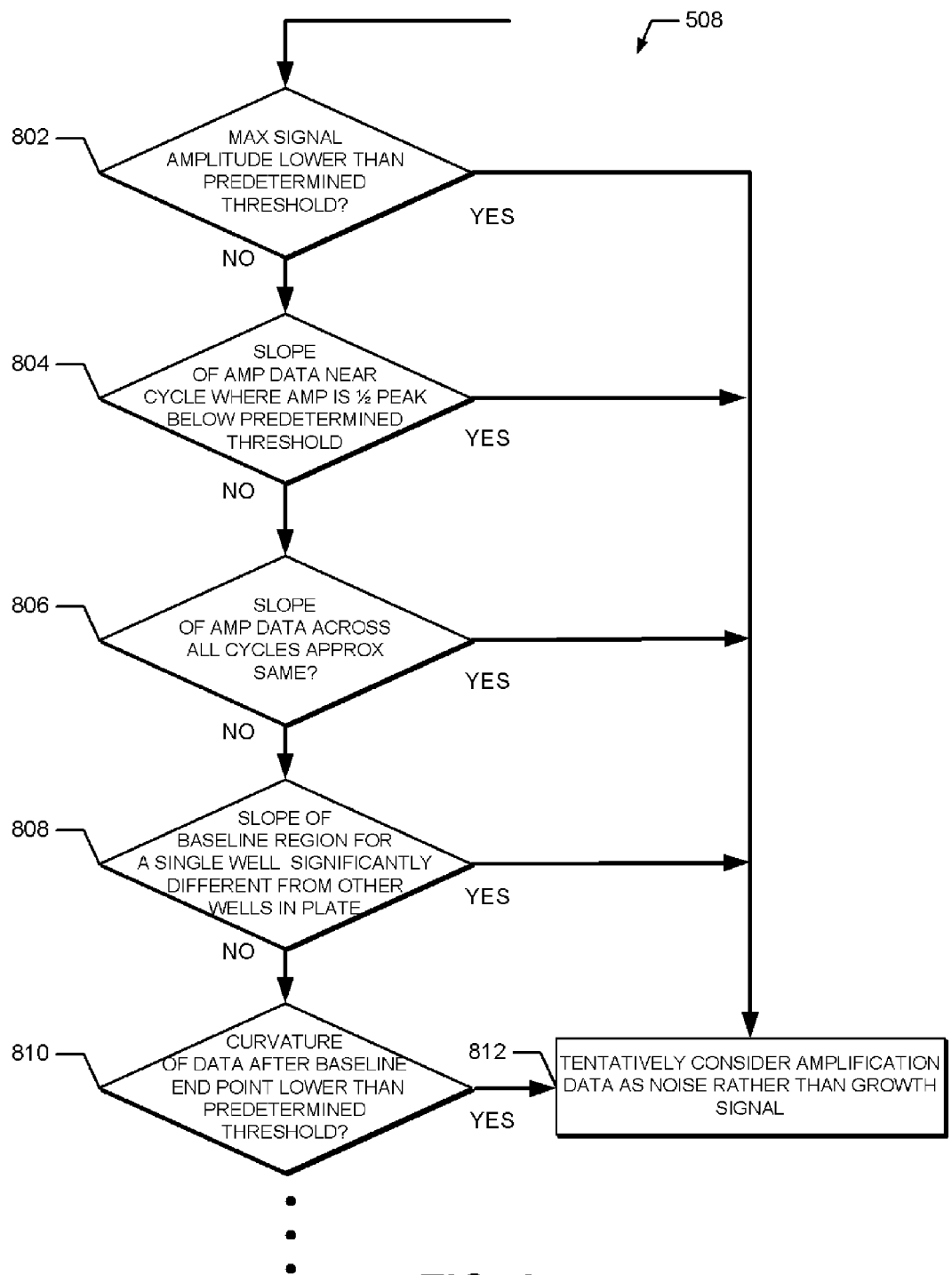
FIG. 8 depicts one or more operations associated with distinguishing putative signals from noise based on the amplification data and in accordance with implementations of the present invention.

FIG. 8 depicts one or more operations associated with distinguishing putative signals from noise based on the amplification data and in accordance with implementations of the present invention. Collectively, these and other types of analysis like these are considered 'noise detectors'. In each of these example operations, a determination of noise leads to tentatively considering the amplification data as noise rather than associated with growth signal. Given additional tests performed for false negatives, the putative noise may subsequently be determined to be actual growth signal associated with growth of the genetic sample and reclassified accordingly.

In this example, noise may be identified when the signal amplitude is too low at portions of the data deviating the most from the signal in the baseline region. (802). For example, the maximum strength of the amplification signal below a predetermined threshold may be considered too low.

Next, a small slope of the amplification data near the cycle where the amplification is approximately ½ the peak may also indicate noise rather than growth signal (804). This measure considers that the slope around this point in the amplification profile should exhibit relative rapid growth of the genetic sample and a somewhat steep slope.

A comparison of slopes across the various amplification data should show a fairly wide variation if true growth is occurring in the genetic sample. Instead, a relatively constant slope in the baseline region, exponential region and plateau region across all cycles indicates little or no growth (806).

Slopes are also compared between wells in a plate to distinguish noise from growth signal data. It is contemplated and observed that the slopes of the baseline region is roughly the same across all wells in a plate. Accordingly, a baseline slope that deviates too much from the mean across the plate may indicate noise (808).

As a last example, noise may also be determined when the curvature of data following the baseline endpoint is too low as measured by the aspect ratio of the amplification data (810). This indicates potential noise (812) because most PCR growth profiles exhibit inhibition following the growth region; this inhibition results in a region of substantial negative curvature.

Figure 9:
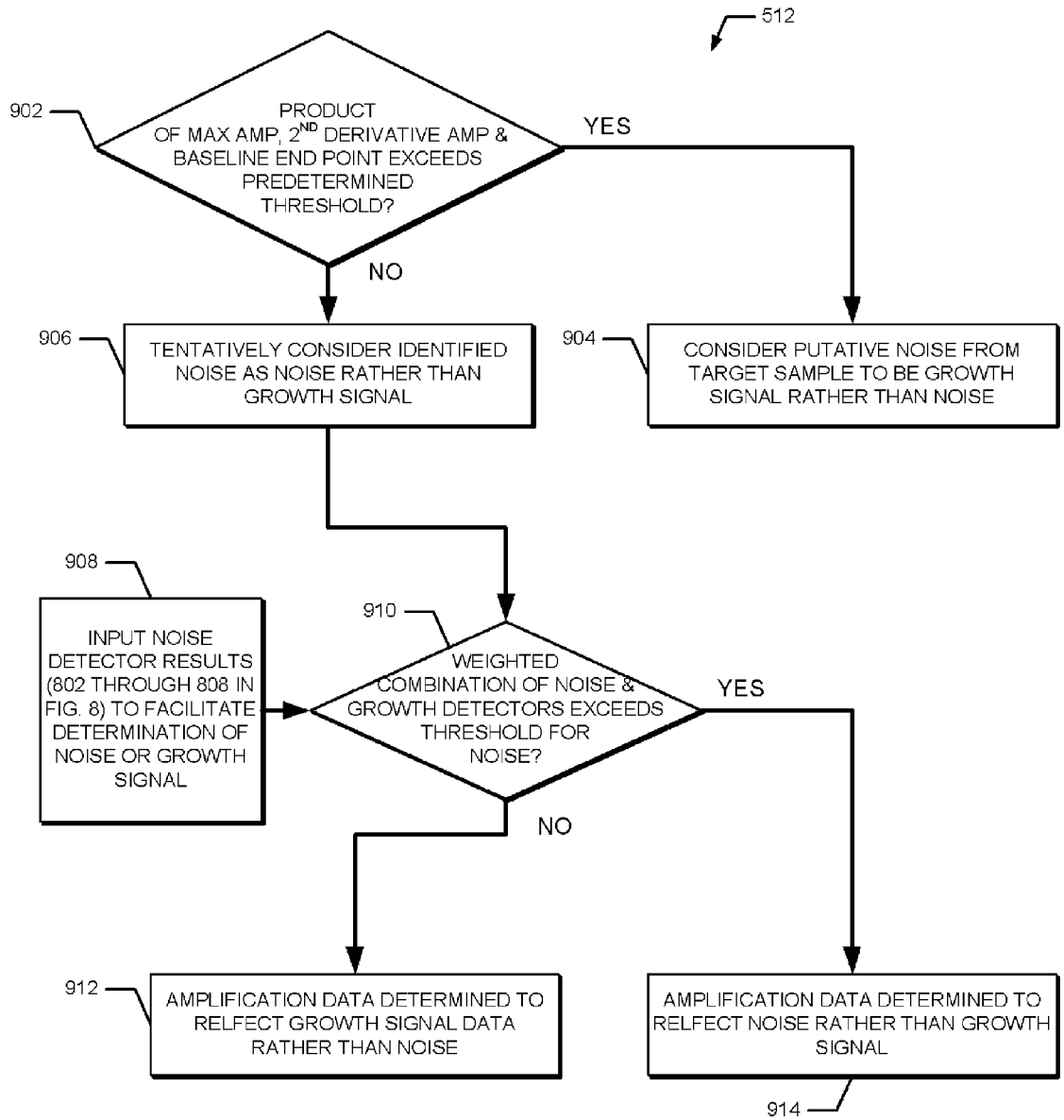
FIG. 9 depicts one or more operations associated with distinguishing putative noise from growth signals based on the amplification data and in accordance with implementations of the present invention.

FIG. 9 depicts one or more operations associated with distinguishing putative noise from growth signals based on the amplification data and in accordance with implementations of the present invention. In each of these example operations, a determination of signal leads to considering the amplification data as signal rather than putative noise as previously determined. By performing these tests for false negatives, amplification data previously considered as putative noise is reconsidered and classified as data exhibiting growth of genetic material.

In one implementation of the invention, an initial determination of putative noise depends on a normalized product of maximum amplification value, a $2^{nd}$ derivative of the amplification data together with a baseline end point. This implementation compares the normalized product of these value against a predetermined threshold (902). The product of these values is one type of 'growth detector' for detecting growth signals. It is contemplated that many other combinations of values derived from one or more derivatives (i.e., $0^{th}$ derivative, $1^{st}$ derivative, $2^{nd}$ derivative . . . $n^{th}$ derivative) of the amplification data, the amplification data itself, the baseline end point can be used to make this initial determination.

Further, one or more indices to recognize growth signal may be derived from features of the amplification data which include, but are not limited to, the number of peaks in the second derivative, the relative position and amplitude of these peaks, the cycle of the baseline end point relative to the length of the signal, and the maximum amplitude of the amplification data relative to baseline variation (902). The index is constructed so that if it exceeds a threshold value then the amplification data is considered to reflect actual growth of the genetic material.

Consequently, in the event the product of these values exceeds the threshold (902), aspects of the present invention considers the putative noise from the target sample or amplification data to be growth signal rather than putative noise (904). Alternatively, if the product of these values does not exceed the threshold (902), then aspects of the present invention considers the putative noise from the target sample or amplification data to more likely be putative noise (906).

An additional analytical operation is then used to make a more final determination whether the putative noise from the amplification data actually corresponds to growth signal and not noise. The second determination is made by constructing a weighted combination of the decisions of the noise detectors (i.e., computed as operations in FIG. 8) and growth detectors computed herein above in FIG. 9. By analogy, aspects of the present invention uses various growth detectors and noise detectors as agents for 'voting' whether the amplification data is noise or growth signal. This heuristic improves overall accuracy by reducing the false negatives and identifying growth signals.

The additional analytical operation creates a weighted combination of noise detector results and compares if the results exceeds a predetermined threshold for noise (910). The noise detector results may be one or more of the noise detector operations previously described in conjunction with FIG. 8, 802 through 808 combined together in a weighted manner as described herein (908). In one implementation, the baseline slope detector (808) and the second derivative growth detector (902) carry the most weight in this determination.

Depending on the result, amplification data is determined to reflect growth signal data rather than noise (912) or amplification data is determined to reflect noise rather than growth signal (914).

If the final decision is that the amplification data is growth signal of genetic material, $C_T$ value is estimated as follows: the threshold for determining the cycle threshold value is considered a predetermined multiple of the variance as measured between the start point and end point of the baseline. The variance may be determined according to the standard deviation in a single well or the population variance/median value as determined by a predetermined set of wells in a plate. Intersection of the cycle threshold amplitude and the amplification data defines the $C_T$ value. To improve accuracy of estimating this intersection, a cubic spline interpolation may be used to fit the amplification data in the vicinity of the intersection.

Application of the aforementioned methods may be used in connection with PCR-based quantification and analysis including real-time applications. Such approaches and instruments may further be useful in finding genetic correlates of disease as well as in quantification and genotyping assays.

Figure 10:
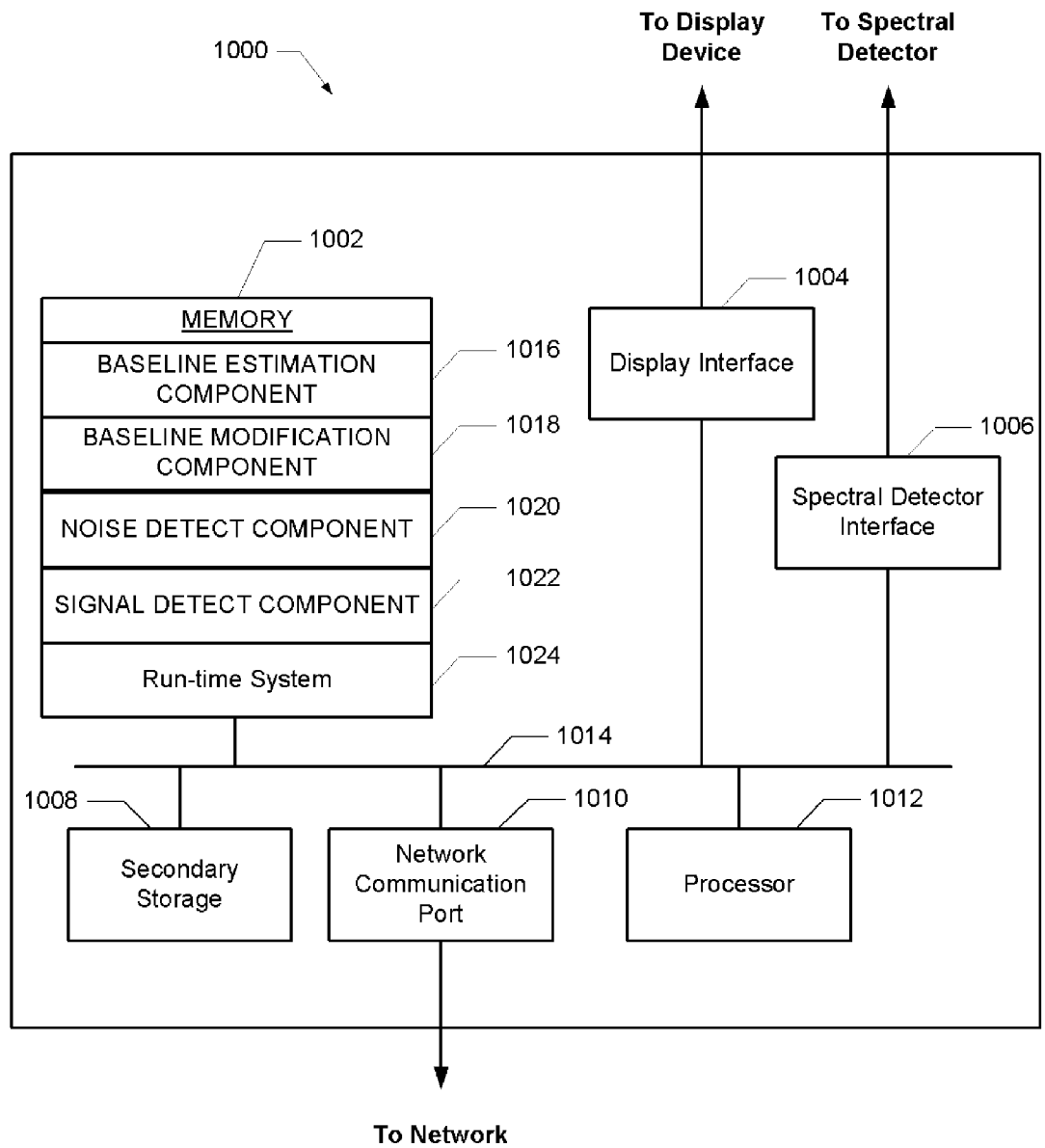
FIG. 10. is a block diagram of a system used in operating an instrument or method in accordance with implementations of the present invention.

FIG. 10 is a block diagram of a system used in operating an instrument or method in accordance with implementations of the present invention. System 1000 includes a memory 1002 to hold executing programs (typically random access memory (RAM) or read-only memory (ROM) such as Flash), a display interface 1004, a spectral detector interface 1006, a secondary storage 1008, a network communication port 1010, and a processor 1012, operatively coupled together over an interconnect 1014.

Display interface 1004 allows presentation of information related to operation and calibration of the instrument on an external monitor. Spectral detector interface 1006 contains circuitry to control operation of a spectral detector including duplex transmission of data in real-time or in a batch operation. Secondary storage 1008 can contain results and programs for long-term storage including one or more baseline estimation and modification factors and other data useful in automating baseline and CT determination using amplification data derived from the spectral detector. Network communication port 1010 transmits and receives results and data over a network to other computer systems and databases. Processor 1012 executes the routines and modules contained in memory 1002.

In the illustration, memory 1002 includes a baseline estimation component 1016, baseline modification component 1018, noise detect component 1020, signal detect component 1022 and a run-time system 1024. Run-time system 1024 manages system resources used when processing one or more of the previously mentioned modules. For example, run-time system 1024 can be a general-purpose operating system, an embedded operating system or a real-time operating system or controller.

System 1000 can be preprogrammed, in ROM for example, using field-programmable gate array (FPGA) technology or it can be programmed (and reprogrammed) by loading a program from another source (for example, from a floppy disk, an ordinary disk drive, a CD-ROM or another computer). In addition, system 1000 can be implemented using customized application specific integrated circuits (ASICs).

Having thus described various implementations and embodiments of the present invention, it should be noted by those skilled in the art that the disclosures are exemplary only and that various other alternatives, adaptations and modifications may be made within the scope of the present invention. For example, various implementations of the invention are described as being used for gene expression however it is contemplated that the processing, analysis and graphical user interface described can be used directly for or adapted for use in genotyping data, allelic discrimination type studies as well as any other type of biological or genetic analysis.

Embodiments of the invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of nonvolatile memory, including by way of example semiconductor memory devices, such as EPROM, EEPROM and flash memory devices; magnetic disks such as internal hard disks and removable disks; magneto-optical disks; and CD-ROM disks. Any of the foregoing can be supplemented by, or incorporated in, ASICs.

Thus, the invention is not limited to the specific embodiments described and illustrated above. Instead, the invention is construed according to the claims that follow and the full scope of their equivalents thereof.

What is claimed is:

1. A computer implemented method of automating analysis of genetic samples, comprising:
   receiving amplification data associated with at least one spectral species and a genetic sample in each well of a plate;
   identifying a putative growth signal for the genetic sample from the amplification data forming a baseline region having a start point and an end point along with a growth region, the identifying a putative growth signal including
      creating the baseline region with a first slope along the amplification data between the start point and the end point, the first slope being significantly less than a second slope along the amplification data associated with the growth region, and
      setting a signal threshold level for determining a cycle threshold (C.sub.T) at a predetermined multiple of the variance in the baseline between the starting point and the endpoint; and
   modifying the baseline region to further identify the putative growth signal depending on one or more characteristics detected in the amplification data forming the baseline region and growth region.

2. A computer implemented method of automating analysis of genetic samples, comprising:
   receiving amplification data associated with at least one spectral species and a genetic sample in each well of a plate;
   identifying a putative growth signal for the genetic sample from the amplification data forming a baseline region having a start point and an end point along with a growth region, the identifying a putative growth signal including creating the baseline region with a first slope along the amplification data between the start point and the end point, the first slope being significantly less than a second slope along the amplification data associated with the growth region, and setting a signal threshold level for determining a cycle threshold ($C_T$) at a predetermined multiple of the variance in the baseline between the starting point and the endpoint, wherein the variance from the baseline is selected from a set including: a standard deviation of the baseline from a single well in the plate and a population variance from multiple wells in the plate; and modifying the baseline region to further identify the putative growth signal depending on one or more characteristics detected in the amplification data forming the baseline region and growth region.

3. The method of claim 2 wherein identifying a putative growth signal having an initial baseline and a growth region further comprises:

measuring a number of zero crossings of the amplification data to determine if the amplification data may correspond to noise; and obviating anomalous data patterns identified in the amplification data that may interfere with finding a starting point and an endpoint for the baseline and the putative growth signal.

4. The method of claim 3 wherein the anomalous data patterns may include one or more patterns selected from a set of anomalous patterns including: early cycles showing significant excursions in fluorescence values compared to later cycles, significant negative amplitude changes in the growth region of amplification data, significant excursions in fluorescence values during a single cycle, starting point of baseline significantly exceeds variation associated with baseline, and growth region of amplification data does not exceed variation associated with baseline.

5. A computer implemented method of automating analysis of genetic samples, comprising:

receiving amplification data associated with at least one spectral species and a genetic sample in each well of a plate;

identifying a putative growth signal for the genetic sample from the amplification data forming a baseline region having a start point and an end point along with a growth region;

determining whether the amplification data reflects putative noise rather than the putative growth signal associated with growth of the genetic sample during amplification by validating the amplification data associated with the baseline region;

determining whether the putative noise from the amplification data reflects an actual growth signal associated with growth of the genetic sample during amplification rather than putative noise by a further validation of the amplification data associated with the baseline region, wherein determining whether the amplification data reflects an actual growth signal rather than putative noise is based upon whether a product of a maximum amplitude of the amplification data, a second derivative of the amplification data and a baseline end point exceed a predetermined threshold; and classifying the amplification data from the genetic sample as an actual growth signal responsive to the further validation of the amplification data associated with the baseline region.

6. The method of claim 5 wherein making a final determination of whether or not amplification data is noise or growth signal is determined by a weighted combination of one or more noise detectors and growth detectors derived from the amplification data.

* * * * *